(12) United States Patent
Son et al.

(10) Patent No.: US 9,447,124 B2
(45) Date of Patent: Sep. 20, 2016

(54) MULTI-THIOL MERCAPTOALKOXYSILANE COMPOSITIONS

(71) Applicant: Southern Methodist University, Dallas, TX (US)

(72) Inventors: David Y. Son, Plano, TX (US); Abby R. Jennings, McKinney, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 14/972,323

(22) Filed: Dec. 17, 2015

(65) Prior Publication Data

US 2016/0130287 A1     May 12, 2016

Related U.S. Application Data

(63) Continuation of application No. 14/051,853, filed on Oct. 11, 2013, now Pat. No. 9,243,006.

(60) Provisional application No. 61/713,166, filed on Oct. 12, 2012.

(51) Int. Cl.
    *C07F 7/04*     (2006.01)
    *C07F 7/18*     (2006.01)
    *C07F 7/02*     (2006.01)

(52) U.S. Cl.
    CPC .......... *C07F 7/184* (2013.01); *C07F 7/02* (2013.01); *C07F 7/188* (2013.01); *C07F 7/1836* (2013.01)

(58) Field of Classification Search
    CPC .......... C07F 7/18; C07F 7/184; C07F 7/188; C07F 7/1836
    USPC ....................................................... 556/429
    See application file for complete search history.

(56) References Cited

U.S. PATENT DOCUMENTS

| | | |
|---|---|---|
| 3,838,096 A | 9/1974 | Nagasawa et al. |
| 5,183,914 A | 2/1993 | Yeh et al. |
| 6,890,605 B2 * | 5/2005 | Nishikawa ............... C23C 18/04 257/E21.261 |
| 7,560,583 B2 | 7/2009 | Chaves et al. |
| 8,008,519 B2 | 8/2011 | Chaves et al. |
| 8,067,459 B2 | 11/2011 | Ashwell et al. |
| 2011/0287205 A1 | 11/2011 | Klockmann et al. |

FOREIGN PATENT DOCUMENTS

WO     2009-132265 A2     10/2009

OTHER PUBLICATIONS

Becker, Von B., et al., Z. Anorg. Allgem Chemie, 1982, vol. 488, pp. 299-334.
Kniess, Torsten, et al., "Synthesis of hydroxyl silylated rhenium and (99mTc)technetium '3+1' mixed ligand complexes," J. Label Compd Radiopharm, vol. 45, Jan. 2002, pp. 629-636.
International Search Report and Written Opinion of FIPS for PCT/US2013/064538 dated Mar. 27, 2014, 13 pp.
Jennings, Abby R., et al., "Multifunctional thiols from the highly selective reaction of mercaptoalcohols with ahlorosilances," Chemical Communications, Mar. 2013, 49 (33), 3467-3469.
Wojnowski, W., et al., "The chemistry of silicon-sulfur compounds, XLIII, Alcoholysis reaction of silicon-sulfur compounds with alkoxyethanols and 2-mercaptoethanol," Zeitschrift fuer Anorganische and Allgemeine Chemie, 1987, 546, pp. 220-234, Abstract.
Zablotskaya, A., et al., "Synthesis and physicochemical characterization of triorganylsiloxyalkyl monodentate ligands with free mercapto group," Latvijas Kimijas Zurnals, Nov. 2001, 4, pp. 339-343.

* cited by examiner

*Primary Examiner* — Porfirio Nazario Gonzalez
*Assistant Examiner* — Kofi Adzamli
(74) *Attorney, Agent, or Firm* — Chainey P. Singleton; Chalker Flores, LLP

(57) ABSTRACT

The present invention provides multi-thiol mercaptoalkoxysilane compositions and methods of making multi-thiol mercaptoalkoxysilane compositions having the formula:

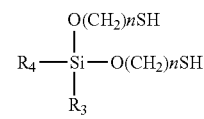

wherein the $R_3$ group, and the $R_4$ group are independently an alkoxy, a halogen, an alkyl, an aryl, a heteroaryl, a heterocycle or derivatives thereof and n is an integer between 1 and 30.

14 Claims, No Drawings

MULTI-THIOL MERCAPTOALKOXYSILANE COMPOSITIONS

CROSS-REFERENCE TO RELATED APPLICATIONS

This patent application is a Continuation Application and claims priority based on U.S. patent application Ser. No. 14/051,853 filed on Oct. 11, 2011 and entitled "Multi-Thiol Mercaptoalkoxysilane Compositions", and U.S. provisional patent application 61/713,166 filed on Oct. 12, 2012 and entitled "Multi-Thiol Mercaptoalkoxysilane Compositions," the contents of each of which are hereby incorporated by reference in its entirety

TECHNICAL FIELD OF THE INVENTION

The present invention relates generally to silanes and methods of making and using those compositions and more specifically to multi-thiol mercaptoalkoxysilane compositions and methods of making and using the same.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with silanes. Silanes including mercaptosilanes are very reactive compounds and this reactivity causes the compositions to be difficult to synthesize and particularly difficult to use in preparing filled elastomer compositions. The chemoselective reaction of chlorosilanes with mercaptoalcohols has been reported (Wada, M. et al, Journal of Organometallic Chemistry 1972, 39, 99-106); however, these compounds contained a single thiol group. Since that time, several articles have described the preparation of similar single-thiol compounds.

For example, U.S. Pat. No. 8,008,519, entitled, "Process for Making Mercapto-Functional Silane," discloses organofunctional silanes and mixtures of organofunctional silanes possessing mercaptan and hydrocarbyl and/or heterocarbyl functionality. These silanes reduce or eliminate the generation of volatile organic compounds during use, aid in the processing of filled elastomeric materials, and enhance the end-use properties of the filled elastomer.

Examples of alkoxysilanes and oligomeric alkoxysiloxanes can be seen in U.S. Pat. No. 5,183,914, entitled, "Alkoxysilanes and Oligomeric Alkoxysiloxanes by a Silicate-Acid Route," disclose a method of preparing alkoxysilanes and oligomeric alkoxysiloxanes by reacting a metal silicate with an acid selected from the group consisting of sulfurous acid and acids with a pKa greater than about 2.5 in the presence of an alcohol. The resultant product is then reacted with an alcohol to form the alkoxysilane or oligomeric alkoxysiloxane, depending on the starting silicate.

An article published in a German journal (Becker, B. et al, Zeitschrift fur anorganische und allgemeine Chemie 1982, 488, 229-234) lists several di-thiol compounds as part of a larger library of compounds but without detailed experimental and characterization data.

A recent patent (WO 2009/132265) describes degradable compounds that possess a silicon bonded to two oxygen atoms; however, the general descriptions include compositions having a different structure and properties and would not include the compounds of the present invention.

SUMMARY OF THE INVENTION

The present invention discloses multi-thiol mercaptoalkoxysilane compositions and methods of making and using the same. For example, the present invention provides a mercaptoalkoxysilane composition comprising the formula:

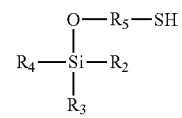

wherein the $R_2$, $R_3$, and $R_4$ groups are independently an alkoxy, a halogen, an alkyl, an aryl, a heteroaryl, a heterocycle or derivatives thereof and the $R_5$ group is an alkyl group having between 1 and 30 carbons. In one embodiment, the $R_5$ group is a $—(CH_2)n—$ group where n is an integer from 1 to 10. For example, the $R_5$ group may be $—CH_2—$, $—CH_2CH_2—$, $—CH_2CH_2CH_2—$, $—CH_2CH_2CH_2CH_2CH_2CH_2CH_2CH_2—$, or a substituted analog or a derivative thereof. In one embodiment, the $R_2$ group is an alkoxy group having the formula $—O(CH_2)nSH$ wherein n is an integer from 1 to 30. The $R_3$ group may be an alkoxy group having the formula $—O(CH_2)nSH$ wherein n is an integer from 1 to 30. The $R_2$ group and the $R_3$ group may be independently an alkoxy group having the formula $—O(CH_2)nSH$ wherein n is an integer from 1 to 30. In one embodiment, the $R_2$ group, the $R_3$ group and the $R_4$ group are alkoxy groups having the formula $—O(CH_2)nSH$ wherein n is independently an integer from 1 to 30. In one embodiment, the $R_2$ group and the $R_3$ group are independently an alkoxy group having the formula $—O(CH_2)nSH$ wherein n is an integer from 1 to 30. In one embodiment, the $R_2$ group, the $R_3$ group and the $R_4$ group are independently an alkoxy group having the formula $—O(CH_2)nSH$ wherein n is an integer from 1 to 30. Specific examples include:

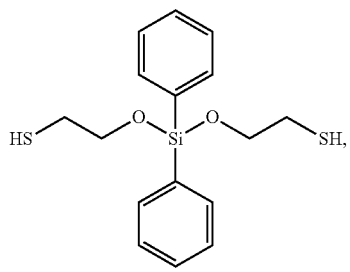

(8)

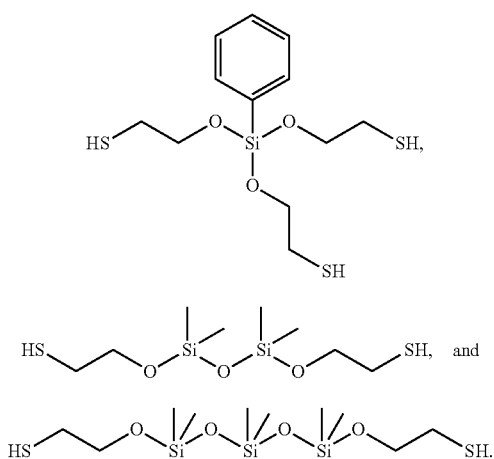

(9)

(10)

(11)

The present invention also provides a mercaptoalkoxysilane composition having the formula:

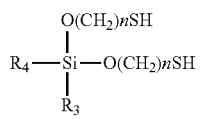

wherein the $R_3$ group, and the $R_4$ group are independently an alkoxy, a halogen, an alkyl, an aryl, a heteroaryl, a heterocycle or derivatives thereof and n is independently an integer between 1 and 30. In one embodiment, n is independently 1, 2, 3, 4, 5, 6, 7 and may also include substituted analogs or derivatives thereof. In another embodiment, the $R_3$ group and the $R_4$ group are independently alkoxy groups having the formula —O(CH$_2$)nSH wherein n is independently an integer from 1 to 30.

The present invention provides a method of making a mercaptoalkoxysilane composition by providing a halogenated silane having at least one halogen; providing at least one mercaptoalcohol having at least one $CH_2$ group and combining the halogenated silane with the at least one mercaptoalcohol in the presence of a base to form a mercaptoalkoxysilane composition. In one embodiment, the halogenated silane comprises at least two halogens, but can have three halogens or four halogens. The at least one mercaptoalcohol may include a first and a second mercaptoalcohol or may include 2, 3, 4 or more different mercaptoalcohols. In one embodiment, the halogenated silane includes at least two halogens and at least a first mercaptoalcohol and a second mercaptoalcohol. The at least one mercaptoalcohol may include 1, 2, 3, 4, 5, 6, 7, 8, 9 or more $CH_2$ groups and may or may not include one or more substitutions.

BRIEF DESCRIPTION OF THE DRAWINGS

None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes branched or unbranched hydrocarbon chains, preferably having about 1 to about 30 carbons, such as, methyl, ethyl, n-propyl, iso-propyl, n-butyl, sec-butyl, iso-butyl, tert-butyl, octadecyl and 2-methylpentyl. These groups can be optionally substituted with one or more functional groups which are attached commonly to such chains, such as hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like. It is understood that the number of carbons may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more, and include branched, multibranched, substituted and linear chains.

The term "alkylene" refers to a divalent alkyl group as defined above, such as methylene (—CH$_2$—), propylene (—CH$_2$CH$_2$CH$_2$—), chloroethylene (—CHClCH$_2$—), 2-thiobutene-CH$_2$CH(SH)CH$_2$CH$_2$, 1-bromo-3-hydroxyl-4-methylpentene (—CHBrCH$_2$CH(OH)CH(CH$_3$)CH$_2$—), and the like.

As used herein, the term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

As used herein, the term "aryl" denotes a chain of carbon atoms which form at least one aromatic ring having between about 4-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl, alkylene, alkenyl, alkynyl, aryl or substituted derivative thereof.

The term "halogen" denotes chlorine, fluorine, bromine, iodine and mixtures thereof.

The term "aryl" denotes an aromatic mono- or bicyclic radical having 5 to 10, preferably 5 to 6 ring atoms, and the term "heteroaryl" includes aryls containing one to three heteroatoms, preferably one heteroatom, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, preferably pyridinyl, isoxazolyl or thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heterocycle" means a straight chain or ring system that may contain from zero to four heteroatoms selected from N, O, and S, wherein the nitrogen and sulfur atoms are optionally oxidized, and the nitrogen atom(s) are optionally quaternized. These groups can be optionally substituted with one or more functional groups as defined under "alkyl" above.

Compounds containing multiple thiol groups (herein referred to as "multi-thiol" compounds) (e.g., —SH functional group is known as a "thiol" or "mercapto" group) consist of a sulfur atom bonded to a hydrogen atom. The natural metal-binding ability of sulfur and the presence of multiple sulfur atoms within each molecule make these compounds valuable for the synthesis of self-assembled monolayers (SAMs) on gold surfaces, the removal of heavy metal contaminants, and the stabilization of metal nanoparticles. Furthermore, the recent development of the thiol-ene reaction has led to application of these compounds as crosslinking agents in plastics technology.

The selection of commercially available multi-thiol compounds is limited and many of the multi-thiol compounds must be synthesized from simpler starting materials. The synthesis of thiols in the art in general is not straightforward, and often involves multiple steps and harsh reaction conditions. Furthermore, the synthesis of thiols in the art is very limited flexibility in terms of controlling the molecular shape or size of the multi-thiol compounds, and also in terms of controlling the overall number of thiol groups on the molecule. The present invention provides a general and versatile synthesis of multi-thiol compounds.

The present invention provides a novel class of multi-thiol mercaptoalkoxysilane compositions and methods of making the same that can be rapidly prepared in high yield. The synthesis of these multi-thiol mercaptoalkoxysilane compositions use readily available starting materials and do not require harsh reaction conditions. Furthermore, a wide variety of multi-thiol mercaptoalkoxysilane structures can be achieved by simply choosing appropriate starting materials. Another unique aspect of the multi-thiol mercaptoalkoxysilane compositions of the present invention is the degradability of these compounds under specific conditions. Thus, for example, degradable plastics can be synthesized using the multi-thiol mercaptoalkoxysilane compositions of the present invention.

One embodiment of the method of synthesis of the multi-thiol mercaptoalkoxysilane compositions of the present invention involves the reaction of a chlorosilane with a mercaptoalcohol in the presence of a base. The general reaction is shown below:

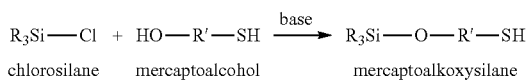

chlorosilane   mercaptoalcohol   mercaptoalkoxysilane

This reaction is remarkable in its chemoselectivity. In contrast to the instant reaction, the skilled artisan would assume the mercaptoalcohol would react through the SH group rather than the OH group since that is the reaction normally seen. As a result, the reaction above and as disclosed herein provides surprising results. In the example shown above, the product contains only one thiol group. The present invention provides an increase in the number of thiol groups in the product by simply choosing a halogenated silane starting material that possesses more than one chlorine (Cl) atom. A specific example is shown below:

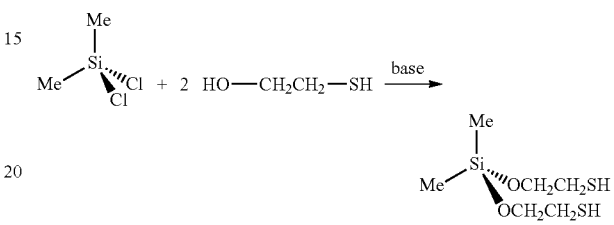

In similar fashion, the present invention provides the following multi-thiol mercaptoalkoxysilanes:

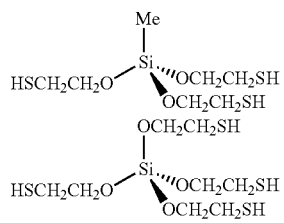

In one example, the reagents were mixed together and stirred overnight at room temperature. The crude product was isolated by filtering off the solid salt byproduct. The product was then purified by distillation.

In general, the present invention provides a multi-thiol mercaptoalkoxysilane composition as seen in the formula below:

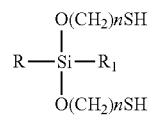

In the formula above each occurrence of n is independently selected from an integer from 1 to 30 and may include straight, cyclic, or branched alkyl, alkenyl, aryl, or alkyl groups that may or may not be unsaturated and may include alkenyl groups, aryl groups, and aralkyl groups, or substitutions thereof. In addition R and $R_1$ may also be independently mercaptoalcohol groups or may include straight, cyclic or branched alkyl, alkenyl, aryl, or aralkyl groups that may or may not be unsaturated and may include alkenyl groups, aryl groups, and aralkyl groups, or substitutions thereof.

In general, the present invention also provides multi-thiol mercaptoalkoxysilane compositions as seen in the formulas below:

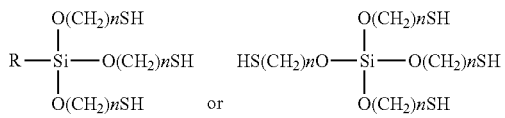

In the formulas above each occurrence of n is independently selected from an integer from 1 to 30 and may include straight, cyclic or branched alkyl, alkenyl, aryl, or alkyl groups that may or may not contain unsaturation and may include alkenyl groups, aryl groups, and alkyl groups, or substitutions thereof. In addition R may also be a mercaptoalcohol group or may include straight, cyclic or branched alkyl, alkenyl, aryl, or alkyl groups that may or may not contain unsaturated bonds and may include alkenyl groups, aryl groups, and alkyl groups, or substitutions thereof.

The present invention demonstrates the versatility of this approach by synthesizing mercaptoalkoxysilanes with different groups attached to the silicon atom, as a non-limiting example:

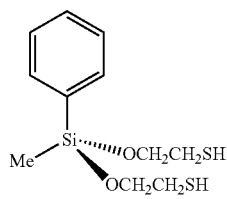

Furthermore, the present invention demonstrates the versatility of this approach by synthesizing mercaptoalkoxysilanes with multiple Si groups attached through an alkyl group or aryl group, or connecting atoms such as O, NH, or other heteroatoms, or combination thereof. For example:

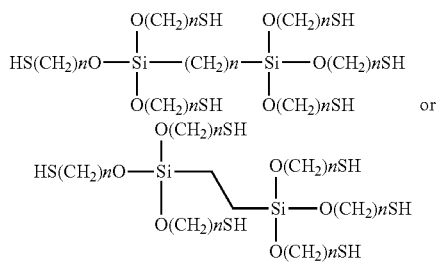

Additionally, different types of mercaptoalcohols can be used in this reaction. For example, multifunctional mercaptoalcohols may be used:

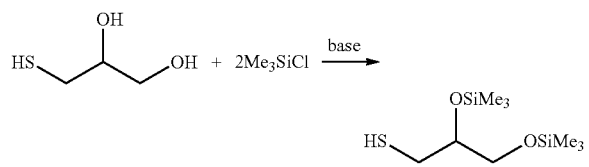

In addition the present invention can further increase the number of thiols and structural diversity in the final product by appropriate choice of the halogenated silane starting material. For example:

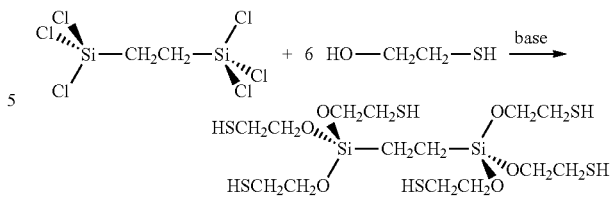

The present invention provides methods of synthesis of compounds in a single day or a few days, controllability of the number of thiol groups, the structure and the type of substituents in the final compound, and the presence of bonds in the final product that can be controllably degraded. These properties provide that the mercaptoalkoxysilanes described herein possess significant potential for widespread use.

As a brief example of potential application, one compound of the present invention was mixed with a commercially available siloxane monomer. Within minutes of mixing under ambient conditions, the mixture solidified to form a clear, colorless rubbery plastic.

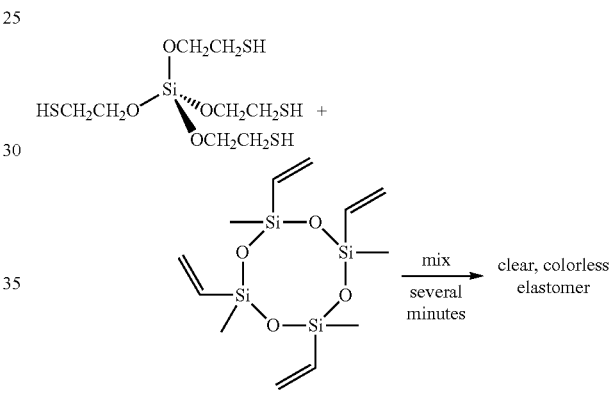

All solvents and reagents were obtained commercially. The chlorosilane starting reagents were distilled over magnesium and the triethylamine was distilled over calcium hydride prior to use. The ether and tetrahydrofuran (THF) were dried using 4 Å molecular sieves.

One example of a compound of the present invention includes a 2-[dimethyl(2-sulfanylethoxy)silyl]oxyethanethiol (1) composition:

(1)

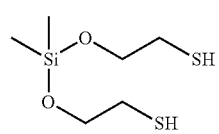

The 2-[dimethyl(2-sulfanylethoxy)silyl]oxyethanethiol composition was synthesized using a 3-necked, 1 L, round bottom flask that was charged with ether (400 mL) and triethylamine (15.68 g, 0.15 mol). Using an overhead mechanical stirrer, the solution was cooled in an ice bath under nitrogen. Dichlorodimethylsilane (10.00 g, 0.077 mol) was added to the stirred solution. The 2-mercaptoethanol (12.10 g, 0.15 mol) was added last. The suspension was gradually warmed to room temperature and stirred under nitrogen overnight. The suspension was vacuum filtered, using ether as a wash. Rotary evaporation was used to remove all volatiles from the filtrate. 2-[dimethyl(2-sulfanylethoxy)silyl]oxyethanethiol (1) was obtained as a clear, colorless, and foul-smelling liquid (16.00 g, 97.2%). The product was purified by distillation under reduced pressure and obtained as a clear, colorless, foul-smelling liquid (12.66 g, 76.9%), Bp=86-87° C. at 1 mmHg.

Another example of a compound of the present invention includes a 2-[methyl-bis(2-sulfanylethoxy)silyl]oxyethanethiol (2) composition:

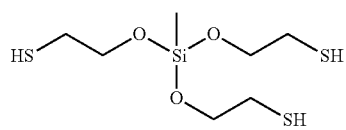

(2)

The 2-[methyl-bis(2-sulfanylethoxy) silyl]oxyethanethiol (2) was synthesized according to the same procedure as 2-[dimethyl(2-sulfanylethoxy)silyl]oxyethanethiol (1), using triethylamine (8.08 g, 0.080 mol), trichloromethylsilane (3.98 g, 0.027 mol), and 2-mercaptoethanol (6.24 g, 0.080 mol) in ether (400 mL). 2-[methyl-bis(2-sulfanylethoxy) silyl]oxyethanethiol (2) was obtained as a clear, colorless, foul-smelling liquid (6.81 g, 93.2%). The product was purified by distillation under reduced pressure and obtained as a clear, colorless, foul-smelling liquid (4.53 g, 62.0%), Bp=128-129° C. at 0.25 mmHg.

Another example of a compound of the present invention includes a tetrakis (2-sulfanylethyl)silicate (3) composition.

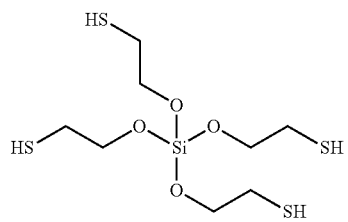

(3)

The tetrakis(2-sulfanylethyl) silicate (3) composition was synthesized according to the same procedure as 2-[dimethyl (2-sulfanylethoxy)silyl]oxyethanethiol (1), using triethylamine (17.27 g, 0.171 mol), tetrachlorosilane (7.25 g, 0.043 mol), and 2-mercaptoethanol (13.33 g, 0.171 mol) in ether (500 mL). The tetrakis(2-sulfanylethyl) silicate composition (3) was obtained as a clear, colorless, foul-smelling liquid (13.64 g, 95.0%). The product was purified by distillation under reduced pressure and obtained as a clear, colorless, foul-smelling liquid (8.56 g, 59.6%), Bp=143-145° C. at 0.05 mmHg.

Another example of a compound of the present invention includes a 2-[methyl-phenyl-(2-sulfanylethoxy)silyl]oxyethanethiol (4) composition:

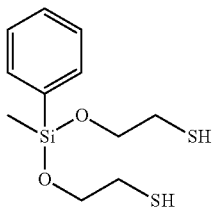

(4)

The 2-[methyl-phenyl-(2-sulfanylethoxy)silyl]oxyethanethiol (4) composition was synthesized according to the same procedure as 2-[dimethyl(2-sulfanylethoxy)silyl] oxyethanethiol (1), using triethylamine (5.02 g, 0.050 mol), dichloromethylphenylsilane (4.74 g, 0.025 mol), and 2-mercaptoethanol (3.88 g, 0.050 mol) in ether (500 mL). The 2-[methyl-phenyl-(2-sulfanylethoxy)silyl]oxyethanethiol (4) composition was obtained as a clear, colorless, foul-smelling liquid (6.30 g, 92.6%). The product was purified by distillation under reduced pressure and obtained as a clear, colorless, foul-smelling liquid (3.70 g, 54.4%), Bp=140-142° C. at 0.50 mmHg.

Another example of a compound of the present invention includes a 2,3-bis(trimethylsilyloxy)propane-1-thiol (5) composition:

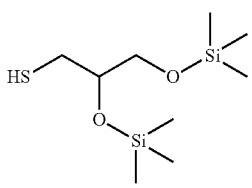

(5)

The 2,3-bis(trimethylsilyloxy)propane-1-thiol (5) composition was synthesized using a 250 mL round bottom flask equipped with a stir bar that was charged with THF (100 mL) and triethylamine (4.35 g, 0.043 mol). The solution was cooled in an ice bath, with stirring, under nitrogen. Trimethylchlorosilane (4.68 g, 0.043 mol) was added to this stirred solution. The α-thioglycerol (2.21 g, 0.020 mol) was added last. The suspension was stirred in an ice bath, under nitrogen, for five minutes. The round bottom flask was then equipped with a reflux condenser and the suspension was heated (~70° C.) in an oil bath under nitrogen overnight. The suspension was cooled to room temperature and vacuum filtered using THF as a wash. Rotary evaporation was used to remove all volatiles from the filtrate. The product was obtained as a clear, faint pink, foul-smelling liquid (5.01 g, 97.1%). The product was purified by distillation under reduced pressure and obtained as a clear, colorless, and foul-smelling liquid (2.15 g, 41.7%), Bp=61-63° C. at 0.50 mmHg.

Another example of a compound of the present invention includes a 2-[bis(2-sulfanylethoxy)-[2-[tris(2-sulfanylethoxy)silyl]ethyl]silyl]oxyethanethiol (6) composition.

(6)

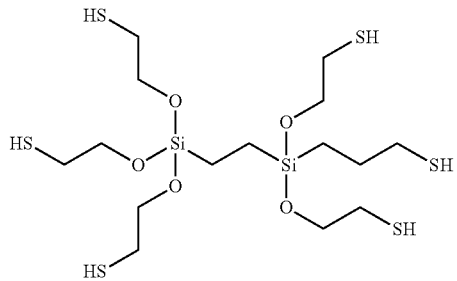

The 2-[bis(2-sulfanylethoxy)-[2-[tris(2-sulfanylethoxy)silyl]ethyl]silyl]oxyethanethiol (6) composition was synthesized by a similar procedure as 2-[dimethyl(2-sulfanylethoxy)silyl]oxyethanethiol (1), using triethylamine (2.7 g, 0.027 mol), trichloro(2-trichlorosilylethyl)silane (1.33 g, 0.0045 mol), and 2-mercaptoethanol (2.09 g, 0.027 mol) in ether (250 mL). The trichloro(2-trichlorosilylethyl)silane was synthesized in house via a hydrosilation reaction with vinyltrichlorosilane and trichlorosilane. The reaction could also be done in THF and similar results are obtained. After vacuum filtering the resulting suspension, all volatiles and unreacted 2-mercaptoethanol were removed by heating (~100° C.) under reduced pressure (0.50 mmHg). The 2-[bis(2-sulfanylethoxy)-[2-[tris(2-sulfanylethoxy)silyl]ethyl]silyl]oxyethanethiol (6) composition was obtained as a hazy, faint orange/brown, foul-smelling viscous liquid (2.40 g, 83.3%).

2-[dimethyl-[2-[tris[2-[dimethyl(2-sulfanylethoxy)silyl]ethyl]silyl]ethyl]silyl]oxyethanethiol (7).

(7)

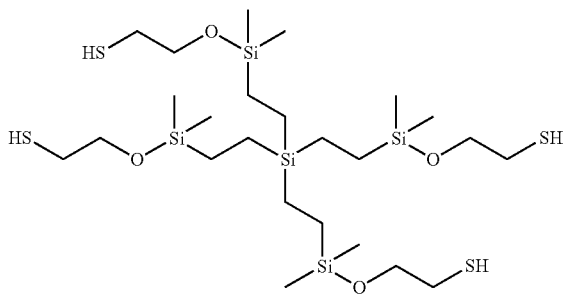

Compound 7 was synthesized according to the same procedure as 2-[dimethyl(2-sulfanylethoxy)silyl]oxyethanethiol (1), using triethylamine (0.96 mL, 0.0069 mol) 2-mercaptoethanol (0.49 mL, 0.0069 mol), and tetrakis[2-[chloro(dimethyl)silyl]ethyl]silane (0.89 g, 0.0017 mol) in ether (30 mL). Tetrakis[2-[chloro(dimethyl)silyl]ethyl]silane was synthesized in house via a hydrosilation reaction with tetravinylsilane and chlorodimethylsilane. The reaction could also be done in THF and similar results are obtained. Compound 7 was obtained as a clear, colorless, foul-smelling liquid (1.15 g, 97.7%). The product was purified by heating (~100° C.) in an oil bath under reduced pressure (0.025 mmHg) to remove any unreacted 2-mercaptoethanol and other impurities. The product was obtained as a clear and colorless, foul-smelling viscous liquid (1.02 g, 86.8%).

The present invention provides multi-thiol compositions and have the general formula:

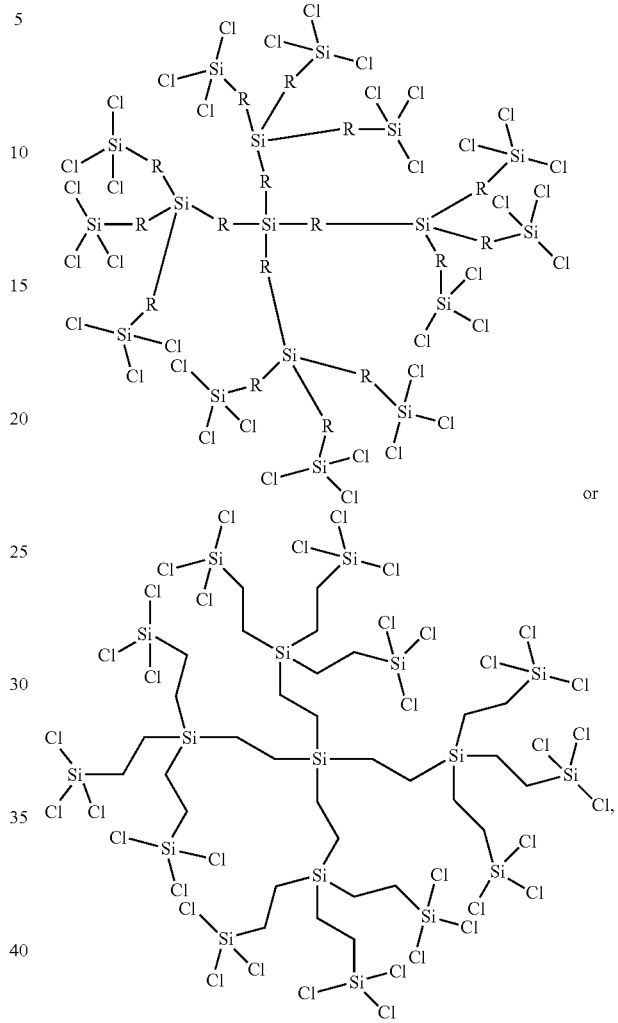

or wherein the R groups may independently be an alkoxy, a halogen, aryl, a heteroaryl, a heterocycle or derivatives thereof or an alkyl, e.g., —$(CH_2)n$— wherein n is preferably an integer from 1 to 30, such as the non-limiting examples of —$CH_2$—, —$CH_2CH_2$—, —$CH_2CH_2CH_2$—, and —$CH_2CH_2CH_2CH_2CH_2CH_2CH_2CH_2$—, and their substituted analogs, such as —$CH_2(CH_2)n*CH(CH_3)$—, where n* is preferably 0 to 16; methyl substituted alkylene groups such as the non-limiting examples of —$CH_2CH_2C(CH_3)_2CH_2$— and —$CH_2CH(CH_3)CH_2$—. $R_4$ may be an alkoxy, a halogen, an aryl, a heteroaryl, a heterocycle or derivatives thereof.

The present invention provides multi-thiol compositions and have the general formula:

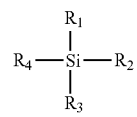

where $R_1$, $R_2$, $R_3$ and $R_4$ are independently an alkoxy, a halogen, aryl, a heteroaryl, a heterocycle or derivatives thereof. For example, when $R_1$, $R_2$, $R_3$ and $R_4$ are independently an alkoxy examples include —OCH$_2$SH, —OCH$_2$CH$_2$SH, —OCH$_2$CH$_2$CH$_2$SH, —OCH$_2$CH$_2$CH$_2$CH$_2$SH, —OCH$_2$CH(CH$_3$)CH$_2$SH, HSCH$_2$CH(CH$_3$)CH$_2$O—, (CH$_3$)$_2$C(O—)CH$_2$CH(SH)CH$_3$, —(CH$_3$)$_2$C(SH)CH$_2$CH(O—)CH$_3$, CH$_3$CH(O—)CH$_2$CH$_2$SH, CH$_3$CH(SH)CH$_2$CH$_2$O—, —OCH$_2$OCH$_2$SH, —OCH$_2$CH$_2$OCH$_2$CH$_2$SH, —OCH$_2$CH$_2$CH$_2$OCH$_2$CH$_2$CH$_2$SH, SHCH$_2$CH(CH$_3$)OCH$_2$CH(CH$_3$)O—, —OCH$_2$CH(CH$_3$)OCH$_2$CH(CH$_3$)SH and —OCH$_2$CH$_2$OCH$_2$CH$_2$OCH$_2$CH$_2$SH. The alkoxy (—OR*—) includes a R* group that may be an alkyl, alkylene, alkenyl, alkynyl, aryl or substituted derivative thereof. The halogen may be chlorine, fluorine, bromine, iodine or mixtures thereof and when multiple R groups are halogens the halogens may be the same or different halogens. The aryl or the heteroaryl groups may be any aromatic or nonaromatic monocyclic or bicyclic composition having 4 to 10, preferably 5 or 6 ring atoms. When in the form of a heteraryl the composition will contain one to three heteroatoms, preferably one heteroatom, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, preferably pyridinyl, isoxazolyl or thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

In the embodiment shown below:

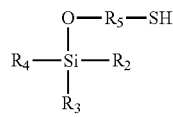

the $R_1$ group is shown as an alkoxy substitution with the R5 group denoting a chain of between 1 and 30 carbons. For example, $R_5$ may have the formula —(CH$_2$)n— wherein n is preferably an integer from 1 to 30, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their substituted analogs, such as —CH$_2$(CH$_2$)n*CH(CH$_3$)—, where n* is preferably 0 to 16; methyl substituted alkylene groups such as the non-limiting examples of —CH$_2$CH$_2$C(CH$_3$)$_2$CH$_2$— and —CH$_2$CH(CH$_3$)CH$_2$—. $R_2$, $R_3$ and $R_4$ may independently be an alkoxy, a halogen, an aryl, a heteroaryl, a heterocycle or derivatives thereof.

In the embodiment shown below:

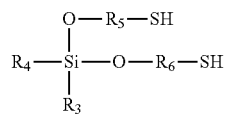

Both the $R_1$ and $R_2$ groups are shown as alkoxy substitutions with the $R_5$ and $R_6$ groups denoting a chain of between 1 and 30 carbons. $R_5$ and $R_6$ may independently have the formula —(CH$_2$)n— wherein n is preferably an integer from 1 to 30, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their substituted analogs, such as —CH$_2$(CH$_2$)n*CH(CH$_3$)—, where n* is preferably 0 to 16; methyl substituted alkylene groups such as the non-limiting examples of —CH$_2$CH$_2$C(CH$_3$)$_2$CH$_2$— and —CH$_2$CH(CH$_3$)CH$_2$—. $R_3$ and $R_4$ are independently an alkoxy, a halogen, an aryl, a heteroaryl, a heterocycle or derivatives thereof.

In the embodiment shown below:

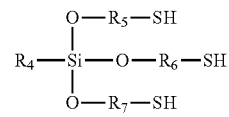

The $R_1$, $R_2$ and $R_3$ groups are shown as alkoxy substitutions with the $R_5$, $R_6$ and $R_7$ groups denoting a chain of between 1 and 30 carbons. $R_5$, $R_6$ and $R_7$ may independently have the formula —(CH$_2$)n— wherein n is preferably an integer from 1 to 30, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their substituted analogs, such as —CH$_2$(CH$_2$)n*CH(CH$_3$)—, where n* is preferably 0 to 16; methyl substituted alkylene groups such as the non-limiting examples of —CH$_2$CH$_2$C(CH$_3$)$_2$CH$_2$— and —CH$_2$CH(CH$_3$)CH$_2$—. $R_4$ may be an alkoxy, a halogen, an aryl, a heteroaryl, a heterocycle or derivatives thereof.

In the embodiment shown below:

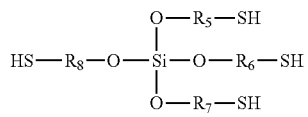

The $R_1$, $R_2$, $R_3$ and $R_4$ groups are shown as alkoxy substitutions with the $R_5$, $R_6$, $R_7$ and $R_8$ groups denoting a chain of between 1 and 20 carbons. $R_5$, $R_6$, $R_7$ and $R_8$ may independently have the formula —(CH$_2$)n— wherein n is preferably an integer from 1 to 30, such as the non-limiting examples of —CH$_2$CH$_2$—, —CH$_2$CH$_2$CH$_2$—, and CH$_2$CH$_2$CH$_2$CH$_2$CH$_2$CH$_2$CH$_2$CH$_2$—, and their substituted analogs, such as CH$_2$(CH$_2$)n*CH(CH$_3$)—, where n* is preferably 0 to 16; methyl substituted alkylene groups such as the non-limiting examples of —CH$_2$CH$_2$C(CH$_3$)$_2$CH$_2$— and —CH$_2$CH(CH$_3$)CH$_2$—.

Other embodiment are shown below:

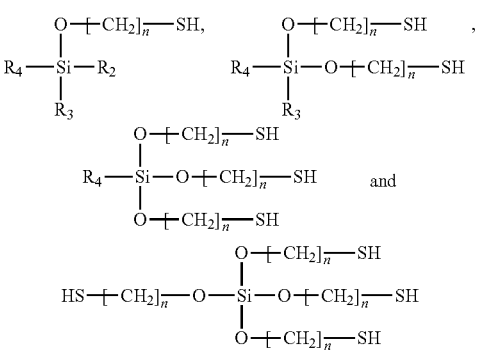

The $R_1$, $R_2$, $R_3$ and $R_4$ groups (when present) are shown as alkoxy groups with a carbon chain of between 1 and 20 carbons present independently as —(CH$_2$)n— wherein n is an integer from 1 to 30, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their substituted analogs, such as —CH$_2$(CH$_2$)n*CH(CH$_3$)—, where n* is preferably 0 to 16; methyl substituted alkylene groups such as the non-limiting examples of —CH$_2$CH$_2$C(CH$_3$)$_2$CH$_2$— and —CH$_2$CH(CH$_3$)CH$_2$—.

The embodiments shown below include a linker between two Si atoms:

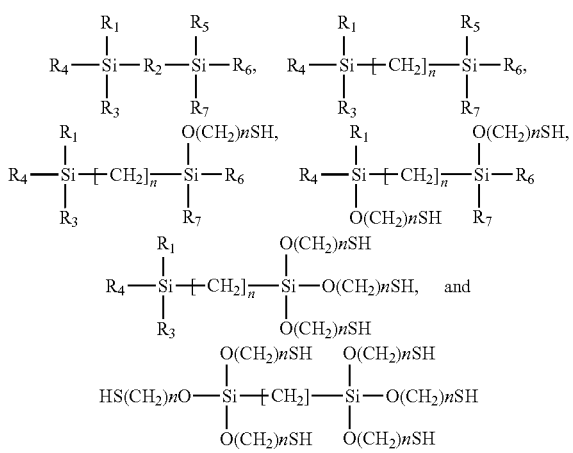

The R$_2$ group denotes a carbon chain of between 1 and 30 carbons. The R$_1$, R$_3$, R$_4$, R$_5$, R$_6$ and R$_7$ groups when present may be independently alkoxy groups or may include straight, cyclic or branched alkyl, alkenyl, aryl, or aralkyl groups that may or may not be unsaturation and may include alkenyl groups, aryl groups, and aralkyl groups, or substitutions thereof. The alkoxy group is shown by the formula —O(CH$_2$)nSH— where n may independently be an integer from 1 to 30, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their substituted analogs, such as —CH$_2$(CH$_2$)n*CH(CH$_3$)—, where n* is preferably 0 to 30; methyl substituted alkylene groups such as the non-limiting examples of —CH$_2$CH$_2$C(CH$_3$)$_2$CH$_2$— and —CH$_2$CH(CH$_3$)CH$_2$—. As used throughout the specification the various R groups are denoted as being a carbon chain of between 1 and 30 carbons and often seen as n denoting between 0 and 30. In these instances the number of carbons (n) may be 1, 2.

For example, specific compositions include 2-[diphenyl (2-sulfanylethoxy)silyl]oxyethanethiol compound (8) below:

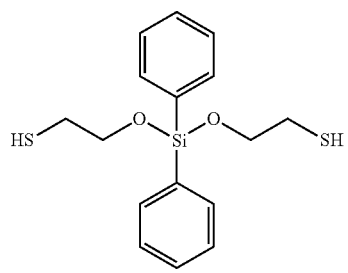

2-[diphenyl(2-sulfanylethoxy)silyl]oxyethanethiol, compound 8 was synthesized according to the same procedure described herein, using triethylamine (9.30 mL, 0.067 mol), 2-mercaptoethanol (4.70 mL, 0.067 mol), and dichlorodiphenylsilane (7.00 mL, 0.033 mol) in ether (200 mL). The product was obtained as a clear and colorless, foul-smelling liquid (10.02 g, 89.5%).

For example, specific compositions include 2-[phenyl-bis (2-sulfanylethoxy)silyl]oxyethanethiol compound (9) below:

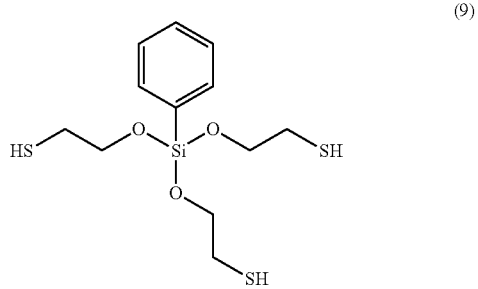 [SMILES: SCCO[Si](OCCS)(OCCS)c1ccccc1]

Compound 9 was synthesized according to the same procedure as 6, using triethylamine (18.20 mL, 0.13 mol), 2-mercaptoethanol (9.20 mL, 0.13 mol), and trichlorophenylsilane (7.00 mL, 0.044 mol) in ether (400 mL). The product was obtained as a clear and colorless, foul-smelling liquid (12.67 g, 86.0%).

For example, specific compositions include 2-[[dimethyl (2-sulfanylethoxy)silyl]oxy-dimethyl-silyl]oxyethanethiol compound (10) below:

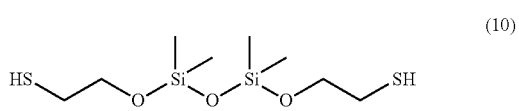

Compound 10 was synthesized according to the same procedure as 6, using triethylamine (9.60 mL, 0.069 mol), 2-mercaptoethanol (4.80 mL, 0.068 mol), and 1,3 dichlorotetramethyldisiloxane (6.80 mL, 0.034 mol) in ether (250 mL). Compound 10 was obtained as a clear, colorless, foul-smelling liquid (9.73 g, 97.3%). The product was purified by heating (~50° C.) in an oil bath under reduced pressure (0.025 mmHg) to remove any unreacted 2-mercaptoethanol and other impurities. The product was obtained as a clear and colorless, foul-smelling viscous liquid (8.90 g, 89%).

For example, specific compositions include 2-[[[dimethyl (2-sulfanylethoxy)silyl]oxy-dimethyl-silyl]oxy-dimethyl-silyl]oxyethanethiol compound (11) below

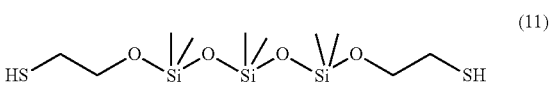 [SMILES: C[Si](C)(OCCS)O[Si](C)(C)O[Si](C)(C)OCCS]

Compound 11 was synthesized according to the same procedure as 6, using triethylamine (7.70 mL, 0.056 mol), 2-mercaptoethanol (3.90 mL, 0.056 mol), and 1,5 dichlorohexamethyltrisiloxane (7.50 mL, 0.027 mol) in ether (200 mL). Compound 11 was obtained as a clear, colorless, foul-smelling liquid (8.58 g, 85.8%). The product was purified by distillation under reduced pressure and obtained as a clear, colorless, foul-smelling liquid (2.21 g, 22.1%), Bp=92-96° C. at 0.050 mmHg.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are incorporated herein by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more items or terms, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. The mercaptoalkoxysilane composition having the formula:

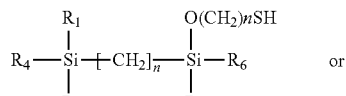

2. A mercaptoalkoxysilane composition comprising the formula:

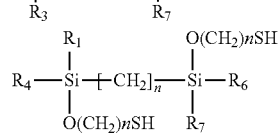

wherein the R1-R6 are independently be a mercaptoalko group, an alkyl, an alkoxy, a halogen, aryl, a heteroaryl, a heterocycle or derivatives thereof, wherein n is 1 to 30.

3. The mercaptoalkoxysilane composition of claim 2, wherein R1, R3, R4, R6 and R7 groups are independently —H, —CH$_3$, —CH$_2$R, —CH$_2$CH$_2$R, —CH$_2$CH$_2$CH$_2$R, —CH$_2$CH$_2$C(CH$_3$)$_2$CH$_2$R, —CH$_2$CH(CH$_3$)CH$_2$R, —CH$_2$CH$_2$CH$_2$CH$_2$CH$_2$CH$_2$CH$_2$CH$_2$R, wherein n is 1 to 30 and R is a —H, —CH$_3$, —SH, or —SiR$_3$ with each of the R in the —SiR$_3$ independently a —H, —CH$_3$, —O(CH$_2$)$_n$R, —O(CH$_2$)$_n$SH, —(CH$_2$)$_n$—, —(CH$_2$)$_n$CH$_3$—, wherein n is 1-30.

4. The mercaptoalkoxysilane composition of claim 2, wherein R1, R3, R4, R5, R6 and R7 groups are independently —O(CH$_2$)$_n$SH, wherein n is 1 to 30.

5. The mercaptoalkoxysilane composition of claim 2, wherein R1, R3, R4, R5, R6 and R7 groups are independently —O(CH$_2$)$_n$R, wherein n is 1 to 30 and R is a —H, —CH$_3$, —SH, —SiR$_3$ with each R of the R3 independently a —O(CH$_2$)$_n$R, —O(CH$_2$)$_n$SH, —(CH$_2$)$_n$—, —(CH$_2$)$_n$CH$_3$, wherein n is 1-30 and R is a —H, —CH$_3$, —SH, or —SiR$_3$.

6. The mercaptoalkoxysilane composition of claim 2, wherein R1, R3, R4, R5, R6 and R7 groups are independently —H, —CH$_3$, —CH$_2$R, —CH$_2$CH$_2$R, —CH$_2$CH$_2$CH$_2$R, —CH$_2$CH$_2$C(CH$_3$)$_2$CH$_2$R, —CH$_2$CH(CH$_3$)CH$_2$R, —CH$_2$CH$_2$CH$_2$CH$_2$CH$_2$CH$_2$CH$_2$CH$_2$R, wherein R is a —H, —CH$_3$, —SH, or —SiR$_3$ with each of the R in the —SiR$_3$ independently a —H, —CH$_3$, —O(CH$_2$)$_n$R, —O(CH$_2$)$_n$SH, —(CH$_2$)$_n$—, —(CH$_2$)$_n$CH$_3$—, wherein n is 1-30.

7. The mercaptoalkoxysilane composition of claim 2, wherein the R1, R3, R4, R6 and R7 groups are independently a mercaptoalkoxysilane composition comprising the formula:

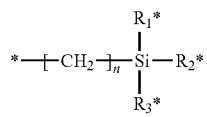

wherein R1*, R2*, and R3* are independently —H, —CH$_2$—R, —CH$_2$CH$_2$—R, —CH$_2$CH$_2$CH$_2$—R, —CH$_2$CH$_2$C(CH$_3$)$_2$CH$_2$—R, —CH$_2$CH(CH$_3$)CH$_2$—R, —CH$_2$CH$_2$CH$_2$CH$_2$CH$_2$CH$_2$CH$_2$CH$_2$—R, —O(CH$_2$)$_n$SH, or substituted analogs thereof and wherein n is 1 to 30 and R is a —H, —CH$_3$, —SH or —SiR$_3$ with each of the R in the —SiR$_3$ independently a —H, —CH$_3$, —O(CH$_2$)$_n$R, —O(CH$_2$)$_n$SH, —(CH$_2$)$_n$—, —(CH$_2$)$_n$CH$_3$—, wherein n is 1-30.

8. A mercaptoalkoxysilane composition comprising the formula:

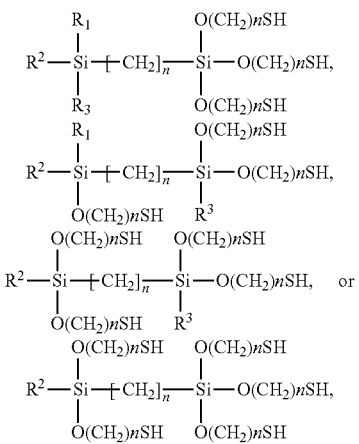

wherein the R groups R1, R2, and R3 are independently a mercaptoalko group, an alkyl, an alkoxy, a halogen, aryl, a heteroaryl, a heterocycle or derivatives thereof, wherein n is 1 to 30.

9. The mercaptoalkoxysilane composition of claim 8, wherein the R1, R2, and R3 groups are independently —H, —CH$_3$, —CH$_2$R, —CH$_2$CH$_2$R, —CH$_2$CH$_2$CH$_2$R, —CH$_2$CH$_2$C(CH$_3$)$_2$CH$_2$R, —CH$_2$CH(CH$_3$)CH$_2$R, —CH$_2$CH$_2$CH$_2$CH$_2$CH$_2$CH$_2$CH$_2$CH$_2$R, wherein n is 1 to 30 and R is a —H, —CH$_3$, —SH, or —SiR$_3$ with each of the R in the —SiR$_3$ independently a —H, —CH$_3$, —O(CH$_2$)$_n$SH, —(CH$_2$)$_n$SiR$_3$—, —(CH$_2$)$_n$CH$_3$—, wherein n is 1-30.

10. The mercaptoalkoxysilane composition of claim 8, wherein the R1, R2, and R3 groups are independently —O(CH$_2$)$_n$SH, wherein n is 1 to 30.

11. The mercaptoalkoxysilane composition of claim 8, wherein the R1, R2, and R3 groups are independently —(CH$_2$)$_n$SiR$_3$, wherein n is 1 to 30 and each R of the R$_3$ is independently a —O(CH$_2$)$_n$R, —O(CH$_2$)$_n$SH, —(CH$_2$)$_n$—, —(CH$_2$)$_n$CH$_3$, wherein n is 1-30 and R is a —H, —CH$_3$, —SH, or —SiR$_3$.

12. A mercaptoalkoxysilane composition comprising the formula:

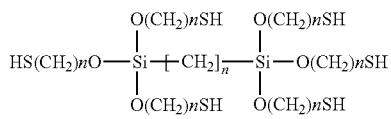

wherein n is independently 1 to 30.

13. A mercaptoalkoxysilane composition comprising the formula:

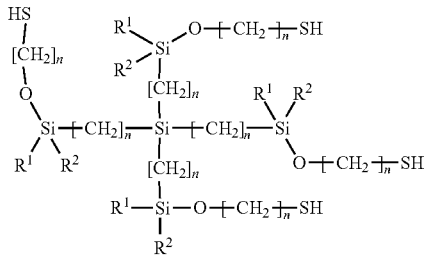

wherein R1 and R2 are independently —H, —CH$_3$, —(CH$_2$)$_n$CH$_3$, —(CH$_2$)$_n$SH, —O(CH$_2$)$_n$SH, —(CH$_2$)$_n$SiR$_3$ with each R of the SiR being a —H, —CH$_3$, or —O(CH$_2$)$_n$SH and n is 1 to 30.

14. The mercaptoalkoxysilane composition having the formula (7)

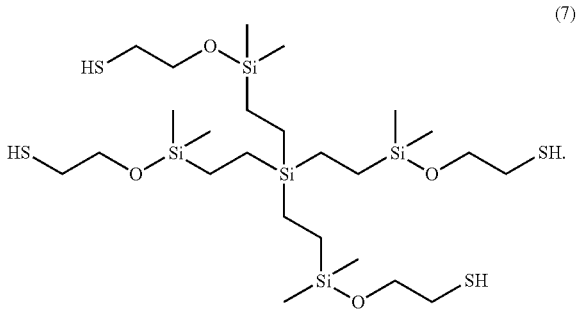 [SMILES: C[Si](C)(CC[Si](CC[Si](C)(C)OCCS)(CC[Si](C)(C)OCCS)CC[Si](C)(C)OCCS)OCCS]

* * * * *